(12) United States Patent
Kale et al.

(10) Patent No.: US 9,226,682 B2
(45) Date of Patent: Jan. 5, 2016

(54) PROCESSING ELECTROCARDIOGRAPH SIGNALS

(71) Applicants: Amit Kale, Karnataka (IN); Venkata Suryanarayana, Karnataka (IN)

(72) Inventors: Amit Kale, Karnataka (IN); Venkata Suryanarayana, Karnataka (IN)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 14/209,477

(22) Filed: Mar. 13, 2014

(65) Prior Publication Data

US 2015/0257672 A1 Sep. 17, 2015

(51) Int. Cl.
*A61N 1/00* (2006.01)
*A61B 5/0472* (2006.01)
*A61B 5/00* (2006.01)

(52) U.S. Cl.
CPC ............. *A61B 5/0472* (2013.01); *A61B 5/7275* (2013.01)

(58) Field of Classification Search
CPC ..................................................... A61B 5/0456
USPC .......................................... 600/521, 509, 523
See application file for complete search history.

(56) References Cited

U.S. PATENT DOCUMENTS

2013/0245480 A1* 9/2013 Crockford ...................... 600/521

OTHER PUBLICATIONS

D. Wyn Davies et al., "Detection of Pathologial Tachycardia by Analysis of Electrogram Morphology", PACE, Mar.-Apr. 1986, pp. 200-208, vol. 9.

Dongping Lin et al., "Identification of Ventricular Tachycardia Using Intracavitary Ventricular Electrograms: Analysis of Time and Frequency Domain Patterns", PACE, Nov. 1988, pp. 1592-1606, Part I.
GE Healthcare, Mac-Lab XTI, General Electric Company, 2014, 4 pages, http://www.gehealthcare.com/euen/cardiology/products/cathlab/hemodynamic_monitoring/cardiolab/cardiolabti.html.
Gordon F. Tomaselli et al., "Morphologic Differences of the Endocardial Electrogram in Beats of Sinus and Ventricular Origin", PACE, Mar. 1988, pp. 254-262, vol. 11.
J.J. Langberg et al., "Identification of Ventricular Tachycardia with Use of the Morphology of the Endocardial Electrogram", Circulation, Journal of the American Heart Association, 1988, pp. 1363-1369, vol. 77.
James F. Kaiser, "On a Simple Algorithm to Calculate the 'Energy' of a Signal", IEEE, 1990, pp. 381-384.
Robert D. Throne et al., "A Comparison of Four New Time-Domain Techniques for Discriminating Monomorphic Ventricular Tachycardia from Sinus Rhythm Using Ventricular Waveform Morphology", IEEE Transactions on Biomedical Engineering, Jun. 1991, pp. 561-570, vol. 38, No. 6.
Robert D. Throne et al., "Use of Tachycardia Templates for Recognition of Recurrent Monomorphic Ventricular Tachycardia", IEEE, 1990, pp. 171-174.

* cited by examiner

*Primary Examiner* — Christopher D Koharski
*Assistant Examiner* — Nadia A Mahmood
(74) *Attorney, Agent, or Firm* — Lempia Summerfield Katz LLC

(57) ABSTRACT

A system for processing electrocardiograph signals includes an interface and a processor. The interface provides a first electrocardiograph signal and a second electrocardiograph signal from an electrocardiograph to the processor. The processor receives the electrocardiograph signals, processes the first electrocardiograph signal to identify a feature of the signal, and processes the second electrocardiograph signal to identify energy over time (e.g., at various time instances), and identifies a first time instance of interest based on the feature.

18 Claims, 2 Drawing Sheets

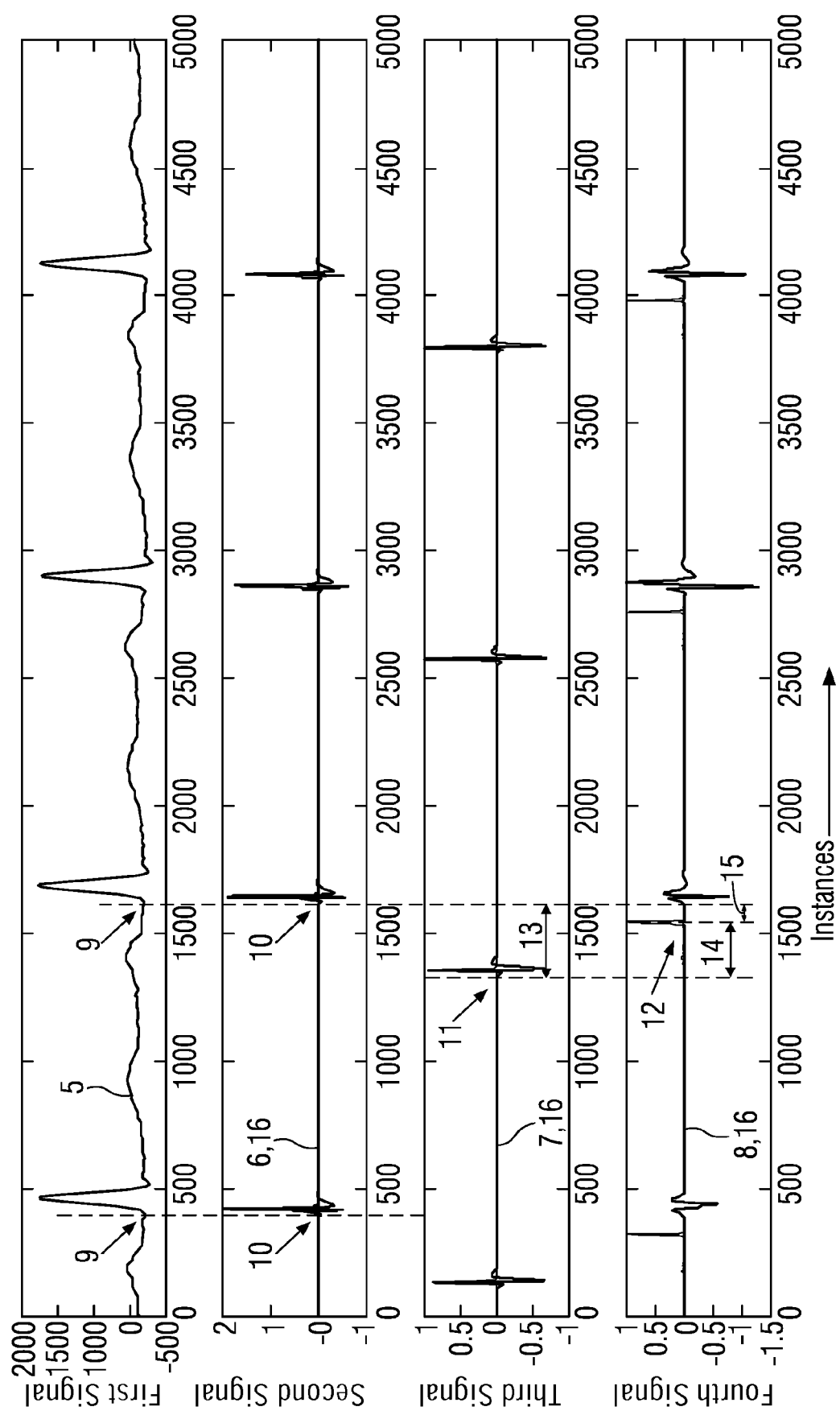

PROCESSING ELECTROCARDIOGRAPH SIGNALS

BACKGROUND

The disclosed embodiments relate to processing an electrocardiograph signal, such as a system for processing an electrocardiograph signal to identify instances of interest in the signal.

Electrocardiography (ECG) is a transthoracic (e.g., across the thorax or chest) interpretation of the electrical activity of the heart over a period of time, as detected by electrodes attached to the outer surface of the skin or at specific loci of the heart via cardiac catheters and recorded by an electrocardiograph external to the body. The electrical activities of the heart are recorded as signals by the electrocardiograph. The signals recorded from the surface of the skin are referred to as surface electrocardiograph signals and the signals from the internal part of the heart are referred to as intracardiac electrograph signals.

ECG with the electrodes at the outer surface of the skin is useful to measure the rate and regularity of heartbeats, the size and position of the chambers, the presence of any damage to the heart, and the effects of drugs or devices used to regulate the heart (such as a pacemaker). While the intracardiac electrograph signals help to detect cardiac arrhythmias, detection of some heart diseases, such as cardiac arrhythmias, involves a great degree of accuracy in identifying few instances of interest in each of the signals. Based on these instances individually and in combination, a physician decides on the occurrence or non-occurrence of the disease in a patient.

One possible way for identifying the instances of interest in signals is by automated segmentation of the signals using frequency and time domain template matching methods, such as correlation waveform analysis, which is independent of amplitude fluctuation and ICE baseline. Correlation waveform analysis is effective in discriminating ventricular depolarizations in sinus rhythm (SR) from indications of ventricular tachycardia (VT), and in differentiating morphologically distinct ventricular tachycardias in the same patient. Another way is based on a difference of area (DOA) scheme, which is dependent upon amplitude fluctuation and ICE baseline. These methods are based on simple criteria, such as the difference of areas between the template and the test signal. The methods have a limitation in connection with the variability in the test signals. The limitation may be met by increasing the number of templates. But incrementing the number of templates leads to increased computation time. Further, these methods implicitly rely on the P wave onset point, which, in some cases, cannot be computed accurately.

SUMMARY

The scope of the present invention is defined solely by the appended claims and is not affected to any degree by the statements within this summary.

A system for processing electrocardiograph signals includes an interface and a processor. The processor provides a first electrocardiograph signal and a second electrocardiograph signal from an electrocardiograph to the processor. The processor receives the electrocardiograph signals, processes the first electrocardiograph signal to identify a feature of the signal, and processes the second electrocardiograph signal to identify energy over time (e.g., at various time instances), and identifies a first time instance of interest based on the feature. Before identifying the energy for each instance of the second signal, the processor smoothes and determines (e.g., finds) a threshold in the second signal.

In one aspect, the first electrocardiograph signal is a surface cardiograph signal and the second signal is an intracardiac electrograph signal.

In one aspect, the feature is a QRS region of the surface electrocardiograph signal.

In one aspect, the processor receives a third electrocardiograph signal from the interface, processes the third signal to identify energy of the third signal at various time instances, and identifies a second time instance of interest based on at least one of the feature and the first time instance.

In one aspect, the processor further measures a first time interval between the first instance of interest and the second instance of interest.

In one aspect, the processor further receives a fourth electrocardiograph signal from the interface, processes the fourth signal to identify energy of the fourth signal at various time instances between the first time interval and identifies a third time instance of interest based on at least one of the feature, the first time instance and the second time instance.

In one aspect, the processor further measures a second time interval between the first instance of interest and the third instance of interest, and measures a third time interval between the third instance of interest and the second instance of interest.

BRIEF DESCRIPTION OF THE DRAWINGS

FIG. 2 illustrates a graphical representation of electrocardiograph signals along with an energy of the signals at each instance of the electrocardiograph signals in accordance with one embodiment.

DETAILED DESCRIPTION

Figure 1:
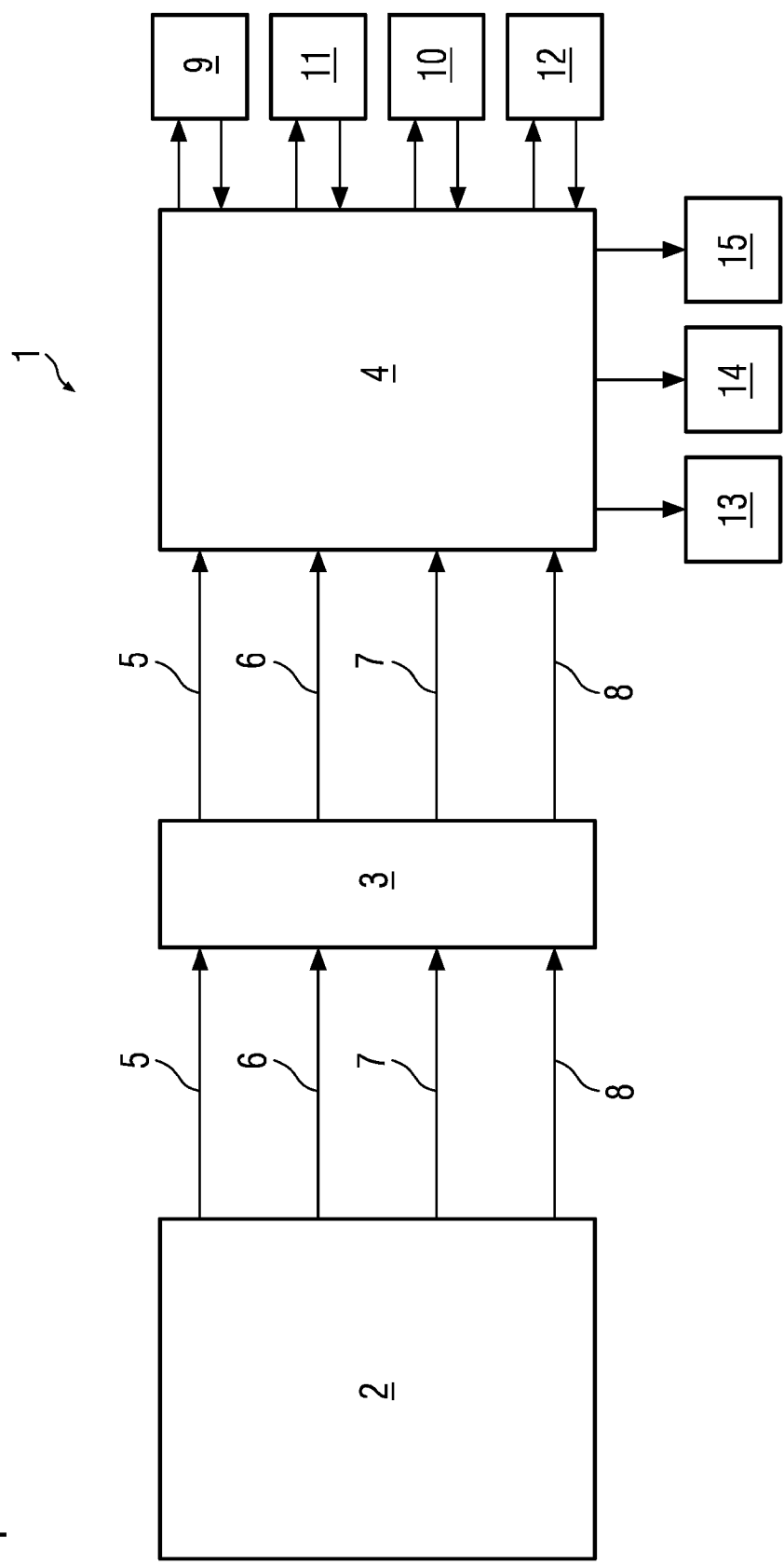
FIG. 1 illustrates a system for processing an electrocardiograph signals in accordance with one embodiment.

FIGS. 1 and 2 are addressed together to describe an embodiment.

FIG. 1 illustrates a system 1 for processing electrocardiograph signals 5, 6, 7, 8. The system 1 includes an electrocardiogram 2 for generating the electrocardiograph signals 5, 6, 7, 8, a processor 4 for processing the electrocardiograph signals 5, 6, 7, 8 and an interface for receiving the electrocardiograph signals 5, 6, 7, 8 from electrocardiogram 2 and for transferring the electrocardiograph signals 5, 6, 7, 8 to the processor 4. The processor uses energy identification for various instances of the signals 6, 7, 8 to process the electrocardiograph signals 6, 7, 8 to provide a first instance 10, a second instance 11 and a third instance 12. Based on the first instance 10, the second instance 11 and the third instance 12, the processor measures a first time interval 13, a second time interval 14 and a third time interval 15. In an alternate embodiment, the processor 4 only processes the first signal 5 and the second signal 6 to identify a feature 9 and the first instance of interest 10. The processor may use any number of such combinations of the first and second signals 5, 6 to identify various first instances 10. Alternatively, the processor 4 only processes the first, second and third signals 5, 6, 7 to identify the feature 9 and the first and second instances of interest 10, 11, and measures first interval 13. In another embodiment, the processor 4 processes the signals 5, 6, 7, 8 to identify feature 9 and the instances of interest 10, 11, 12 and need not measure the time intervals 13, 14, 15.

The electrocardiogram 2 is a device to capture electrical activity of the heart of a human body. The electrical activity is captured using electrodes maintained on the surface of the skin of the human body, as well as through electrodes placed on various parts of the heart inside the human body via catheter.

The processor is a computing unit that receives electrocardiograph signals 5, 6, 7, 8 from the electrocardiogram 2 via the interface 3 and processes the signals to identify the first, second and third instances of interest 10, 11, 12 in the electrocardiograph signals 6, 7, 8, respectively, and also measures the time intervals 13, 14, 15 from the first, second and third instances of interest 10, 11, 12. The processor 4 may also be any general purpose computer adapted to function for processing the signals 5, 6, 7, 8, identifying the instances of interest 10, 11, 12, and measuring the time intervals 13, 14, 15.

The interface 3 is a device that may receive and transfer the electrocardiograph signals 5, 6, 7, 8. Alternatively, the interface 3 may be enabled to transfer a data representation of the signals 5, 6, 7, 8. Alternatively, the interface 3 may be enabled to receive the signals 5, 6, 7, 8 in an electric form (e.g., format), convert the signals from the electric form into a data form (e.g., format), and further transfer the signals 5, 6, 7, 8 into the data form.

The electrocardiograph signals 5, 6, 7, 8 may be surface electrocardiograph signals or intracardiac electrograph signals. The surface electrocardiograph signals are generated by the electrocardiogram 2 from the inputs received via (e.g., out of) leads placed (e.g., put) on the surface of the skin of a human body. The intracardiac electrograph signals are generated by the electrocardiogram 2 from the inputs received via (e.g., out of) leads placed into different areas of the heart of the human body. In one embodiment, the first signal 5 is the surface electrocardiograph signal and the second, third and fourth signals 6, 7, 8 are the intracardiac electrograph signals. The intracardiac electrograph signals may be any of high right atrium (HRA), coronary sinus proximal (CS), right ventricle (RV), His bundle proximal, His Bundle distal, or any other intracardiac electrograph signals that may be captured and recorded by the electrocardiogram 2.

The processor 4 uses the Teager energy approach to identify the energy 16 and to process the second, third and forth signals 6, 7, 8 based on the energy 16 by mapping the energy 16 on the electrocardiograph signals 6, 7, 8. In the Teager energy approach, the electrocardiograph signals 5, 6, 7, 8 are represented by:

$$\sin x(t) = A \sin(\omega t) \quad (I)$$

A Teager energy operator to be applied to the signals 5, 6, 7, 8 by the processor is represented by:

$$\phi[x(t)] = x(t)^2 - x(t)\ddot{x}(t) = A^2\omega^2 \quad (II)$$

The discrete approximation of the equation (II) is represented by:

$$\phi[x[n]] = x[n]^2 - x[n+1]x[n-1] = A^2\omega^2 \quad (III)$$

It follows from the above expressions that the instantaneous energy 6 of the signals 6, 7, 8 is mainly affected by the frequency and amplitude of the signal 6, 7, 8 at that instance. In one embodiment, the instances of interest 10, 11, 12 are identified when no stimulation pulse is applied in the RR interval and at least one of the second, third and fourth signals is available from the right atrium or coronary sinus. The processor may be adapted for cases in which one or more antegrade stimulation pulses are applied in the RR interval with stimulation at the right atrium or coronary sinus. In one diagnosis case, the measurements of interest include the AH, HV and AV intervals, e.g., first, second and third interval 13, 14, 15.

For determining the AH, HV and AV intervals, the processor identifies the instances of interest A, H and V, e.g., the first, second and third instances of interest 10, 11, 12. Further, the QRS complex is the feature 9 identified by the processor 4 from the first signal 5, and the first signal is the surface electrocardiograph signal from the electrode placed onto the surface of the human body.

The processor 4 processes the first electrocardiograph signal 5 to identify the feature 9, e.g., the QRS complex of the signal, and further processes the second electrocardiograph signal 6 to identify the energy 16 at various time instances and identifies the first time instance of interest 10, e.g., V, based on the feature 9. The processor 4 maps the feature 9 onto one of the instances of the second signal 6 and examines a neighborhood of the mapped instance and identifies the first time instance of interest 10, in accordance with the energy 16 in the neighborhood of the mapped instance. The processor 4 uses the Teager energy operator defined in equation (II) or equation (III) for identifying energy at various instances of the second signal 6. Before identifying the energy 16 at various instances, the processor 4 smoothes and determines (e.g., finds) the threshold in the second signal 6.

Further, the processor 4 processes the third signal 7 to identify the energy 16 of the third signal 7 at various time instances using the Teager energy operator as represented in equation (II) or (III). Before identifying the energy 16, the first instance of interest 10 is mapped onto the third signal 7, and the energy 16 is identified for the mapped instance of the third signal and V point of the third signal 7. Further, the processor 4 identifies a second time instance of interest 11, e.g., A, based on at least one of the feature 9 and the first time instance 10, e.g., V. The processor 4 further measures the first time interval 13 between the first instance of interest 10 and the second instance of interest 11, e.g., AV. Before identifying the energy 16 at various instances, the processor 4 smoothes and determines (e.g., finds) the threshold in the third signal 7.

Next, the processor 4 processes the fourth signal 8 to identify the energy 16 of the fourth signal 8 at various time instances between the first time interval 13 and to identify a third time instance of interest 12, e.g., H, based on at least one of the feature 9, the first time instance 10 and the second time instance 11. The processor further measures the second time interval 14, e.g., AH, between the third instance of interest 12 and the second instance of interest 11, and measures the third time interval 15, e.g., HV, between the first instance of interest 10 and the third instance of interest 12. Before identifying the energy 16 at various instances, the processor 4 smoothes and determines (e.g., finds) the threshold in the fourth signal 8.

With continued reference to FIG. 1, FIG. 2 depicts a graphical representation of the electrocardiograph signals 5, 6, 7, 8 on the Y axis and time instances on the X axis. Each of the signals 5, 6, 7, 8 is represented by different graphs including mapping of energy 16 on each of the signals 5, 6, 7, 8. When the processor 4 processes the first signal 5, the processor 4 identifies the feature 9, e.g., the QRS complex. Further, the processor 4 uses the feature 9 and the second signal 6 to identify the first instance of interest 10. The first instance of interest 10 is identified by mapping the energy 16 onto the second signal 6. The first instance of interest 10 is positioned where the energy 16 exhibits a sharp rise on the positive side of the Y axis. The processor 4 uses the first instance of interest 10 and maps the first instance onto the third signal 7 and identifies the second point of instance 11 as where the energy 16 exhibits a sharp rise on the positive side of the Y axis. The processor 4 also measures the first interval 13 between the first and second instances of interest 10, 11. The processor further processes the fourth signal 8 by mapping the first interval 13 onto the fourth signal and identifies the third instance of interest 12 where the energy 16 exhibits a sharp rise on the positive side of the Y axis. The processor also measures the second time interval 14 between the third instance of interest 12 and the second instance of interest 11, and measures the third time interval 15 between the first instance of interest 10 and the third instance of interest 12.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

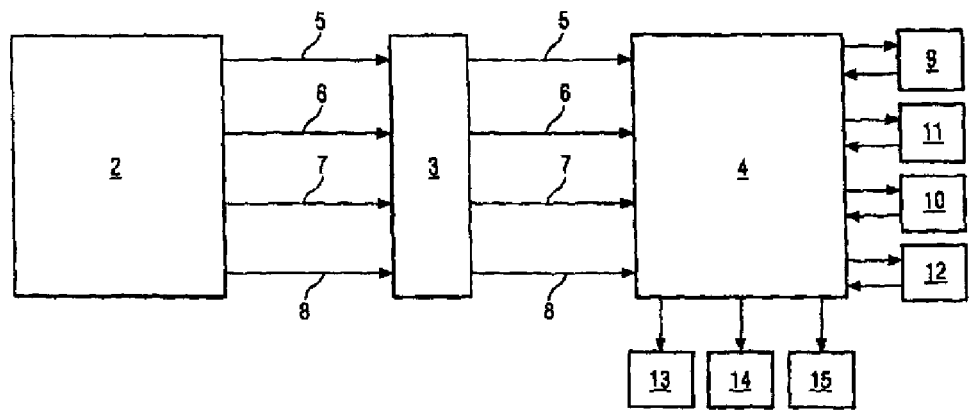

The invention claimed is:

1. A system for processing electrocardiograph signals, the system comprising:
   a processor; and
   an interface to provide a first electrocardiograph signal and a second electrocardiograph signal from an electrocardiograph to the processor,
   wherein the processor is configured to receive the electrocardiograph signals, to process the first electrocardiograph signal to identify a feature of the first electrocardiograph signal, to process the second electrocardiograph signal to identify energy over time, and to identify a first time instance of interest based on the feature, and
   wherein the processor identifies the energy over time by smoothing and determining a threshold in the second electrocardiograph signal.

2. The system of claim 1, wherein the first electrocardiograph signal is a surface cardiograph signal.

3. The system of claim 2, wherein the feature is a QRS region of the surface electrocardiograph signal.

4. The system of claim 1, wherein the second electrocardiograph signal is an intracardiac electrograph signal.

5. The system of claim 1, wherein the interface is configured to provide a third electrocardiograph signal to the processor and wherein the processor is configured to receive the third electrocardiograph signal, to process the third electrocardiograph signal to identify energy of the third electrocardiograph signal over time, and to identify a second time instance of interest based on at least one of the feature and the first time instance.

6. The system of claim 5, wherein the processor is further configured to measure a first time interval between the first instance of interest and the second instance of interest.

7. The system of claim 6, wherein the processor is further configured to receive a fourth electrocardiograph signal, to process the fourth electrocardiograph signal to identify energy of the fourth electrocardiograph signal over time within the first time interval and to identify a third time instance of interest based on at least one of the feature, the first time instance, and the second time instance.

8. The system of claim 7, wherein the processor is further configured to measure a second time interval between the first instance of interest and the third instance of interest, and to measure a third time interval between the third instance of interest and the second instance of interest.

9. A method of processing electrocardiograph signals, the method comprising:
   providing a first electrocardiograph signal and a second electrocardiograph signal from a electrocardiograph to a processor;
   processing the first electrocardiograph signal by the processor to identify a feature of the first electrocardiograph signal; and
   processing the second electrocardiograph signal by the processor to identify energy over time by smoothing and determining a threshold in the second electrocardiograph signal and to identify a first time instance of interest based on the feature.

10. The method of claim 9, further comprising:
    transferring a third electrocardiograph signal to the processor by the interface,
    processing the third electrocardiograph signal by the processor to identify energy of the third electrocardiograph signal over time and to identify a second time instance of interest based on at least one of the feature and the first time instance.

11. The method of claim 10, further comprising:
    measuring a first time interval between the first instance of interest and the second instance of interest by the processor.

12. The method of claim 11, further comprising:
    transferring a fourth electrocardiograph signal to the processor by the interface; and
    processing the fourth electrocardiograph signal by the processor to identify energy of the fourth electrocardiograph signal over time within the first time interval and to identify a third time instance of interest on a basis of at least one of the feature, the first time instance, and the second time instance.

13. The method of claim 12, further comprising:
    measuring a second time interval between the first instance of interest and the third instance of interest by the processor, and
    measuring a third time interval between the third instance of interest and the second instance of interest by the processor.

14. The method of claim 13, wherein the first, second, and third time intervals are the AH, HV, and AV intervals.

15. The system of claim 8, wherein the first, second, and third time intervals are the AH, HV, and AV intervals.

16. The method of claim 9, wherein the first, second, and third intervals are the AH, HV, and AV intervals.

17. The system of claim 1, wherein the first, second, and third intervals are the AH, HV, and AV intervals.

18. The system of claim 1, wherein the interface is configured to receive the first and second electrocardiograph signals in an electric form and to convert the first and second electrocardiograph signals from the electric form into a data form.

* * * * *

UNITED STATES PATENT AND TRADEMARK OFFICE
CERTIFICATE OF CORRECTION

Page 1 of 2

PATENT NO. : 9,226,682 B2
APPLICATION NO. : 14/209477
DATED : January 5, 2016
INVENTOR(S) : Amit Kale and Venkata Suryanarayana It is certified that error appears in the above-identified patent and that said Letters Patent is hereby corrected as shown below:

Delete Title page, and replace with new Title page. (attached)

In the claims
In column 6, delete claims 16 and 17, and renumber claims 1-18 to 1-16.

Signed and Sealed this
Nineteenth Day of April, 2016

Michelle K. Lee
*Director of the United States Patent and Trademark Office*

United States Patent
Kale et al.

(10) Patent No.: US 9,226,682 B2
(45) Date of Patent: Jan. 5, 2016

(54) PROCESSING ELECTROCARDIOGRAPH SIGNALS

(71) Applicants: Amit Kale, Karnataka (IN); Venkata Suryanarayana, Karnataka (IN)

(72) Inventors: Amit Kale, Karnataka (IN); Venkata Suryanarayana, Karnataka (IN)

(73) Assignee: Siemens Aktiengesellschaft, München (DE)

(*) Notice: Subject to any disclaimer, the term of this patent is extended or adjusted under 35 U.S.C. 154(b) by 0 days.

(21) Appl. No.: 14/209,477

(22) Filed: Mar. 13, 2014

(65) Prior Publication Data
US 2015/0257672 A1    Sep. 17, 2015

(51) Int. Cl.
*A61N 1/00* (2006.01)
*A61B 5/0472* (2006.01)
*A61B 5/00* (2006.01)

(52) U.S. Cl.
CPC .......... *A61B 5/0472* (2013.01); *A61B 5/7275* (2013.01)

(58) Field of Classification Search
CPC ............................................. A61B 5/0456
USPC ................................. 600/521, 509, 523
See application file for complete search history.

(56) References Cited

U.S. PATENT DOCUMENTS

2013/0245480 A1* 9/2013 Crockford ............ 600/521

OTHER PUBLICATIONS

D. Wyn Davies et al., "Detection of Pathological Tachycardia by Analysis of Electrogram Morphology", PACE, Mar.-Apr. 1986, pp. 200-208, vol. 9.

Dongping Lin et al., "Identification of Ventricular Tachycardia Using Intracavitary Ventricular Electrograms: Analysis of Time and Frequency Domain Patterns", PACE, Nov. 1988, pp. 1592-1606, Part I.
GE Healthcare, Mac-Lab XTi, General Electric Company, 2014, 4 pages, http://www.gehealthcare.com/euen/cardiology/products/cathlab/hemodynamic_monitoring/cardiolab/cardiolabti.html.
Gordon F. Tomaselli et al., "Morphologic Differences of the Endocardial Electrogram in Beats of Sinus and Ventricular Origin", PACE, Mar. 1988, pp. 254-262, vol. 11.
J.J. Langberg et al., "Identification of Ventricular Tachycardia with Use of the Morphology of the Endocardial Electrogram", Circulation, Journal of the American Heart Association, 1988, pp. 1363-1369, vol. 77.
James F. Kaiser, "On a Simple Algorithm to Calculate the 'Energy' of a Signal", IEEE, 1990, pp. 381-384.
Robert D. Throne et al., "A Comparison of Four New Time-Domain Techniques for Discriminating Monomorphic Ventricular Tachycardia from Sinus Rhythm Using Ventricular Waveform Morphology", IEEE Transactions on Biomedical Engineering, Jun. 1991, pp. 561-570, vol. 38, No. 6.
Robert D. Throne et al., "Use of Tachycardia Templates for Recognition of Recurrent Monomorphic Ventricular Tachycardia", IEEE, 1990, pp. 171-174.

* cited by examiner

*Primary Examiner* — Christopher D Koharski
*Assistant Examiner* — Nadia A Mahmood
(74) *Attorney, Agent, or Firm* — Lempia Summerfield Katz LLC

(57) ABSTRACT

A system for processing electrocardiograph signals includes an interface and a processor. The interface provides a first electrocardiograph signal and a second electrocardiograph signal from an electrocardiograph to the processor. The processor receives the electrocardiograph signals, processes the first electrocardiograph signal to identify a feature of the signal, and processes the second electrocardiograph signal to identify energy over time (e.g., at various time instances), and identifies a first time instance of interest based on the feature.

16 Claims, 2 Drawing Sheets